United States Patent
Farag (10) Patent No.: US 9,241,818 B2
(45) Date of Patent: Jan. 26, 2016

(54) DELIVERY DEVICE HAVING A VARIABLE DIAMETER INTRODUCER SHEATH

(75) Inventor: Jacqueline Farag, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 446 days.

(21) Appl. No.: 13/564,423

(22) Filed: Aug. 1, 2012

(65) Prior Publication Data

US 2013/0035749 A1 Feb. 7, 2013

Related U.S. Application Data

(60) Provisional application No. 61/514,241, filed on Aug. 2, 2011.

(51) Int. Cl.
*A61F 2/06* (2013.01)
*A61F 2/966* (2013.01)
*A61F 2/95* (2013.01)

(52) U.S. Cl.
CPC ......... *A61F 2/966* (2013.01); *A61F 2002/9517* (2013.01); *A61F 2002/9522* (2013.01); *A61F 2250/001* (2013.01); *A61F 2250/0039* (2013.01)

(58) Field of Classification Search
CPC ............ A61F 2/966; A61F 2002/9517; A61F 2002/9522; A61F 2250/001; A61F 2250/0039; A61F 2/02; A61F 2/04; A61F 2/148; A61F 2/1662–2/1678; A61F 2/2427; A61F 2/243; A61F 2/2436; A61F 2/95; A61F 2/954; A61F 2/962; A61F 2002/9528–2002/9534; A61F 2002/9665

USPC ................ 606/108, 191–200; 623/1.11, 1.12, 623/1.23, 2.11
See application file for complete search history.

(56) References Cited

U.S. PATENT DOCUMENTS

| 4,243,040 A | * | 1/1981 | Beecher | 606/127 |
| 4,321,915 A | * | 3/1982 | Leighton et al. | 600/114 |
| 4,863,440 A | * | 9/1989 | Chin | 604/271 |

(Continued)

FOREIGN PATENT DOCUMENTS

| WO | WO 01/35862 A1 | 5/2001 |
| WO | WO 2008/042311 A1 | 4/2008 |

OTHER PUBLICATIONS http://www.thefreedictionary.com/tubular, definition of the term tubular, retrieved Feb. 2015.*

(Continued)

*Primary Examiner* — David C Eastwood
(74) *Attorney, Agent, or Firm* — Brinks Gilson & Lione (57) ABSTRACT

An introducer sheath has a tubular structure that is expandable and contractible to a desired diameter. In a first configuration, the tubular structure has a first diameter and a first axial length. In a second configuration, the tubular structure has a larger second diameter and a shorter second axial length. An actuator includes an inner member and an outer member. In response to relative movement between the members and the tubular structure in a first or second direction, the actuator allows the tubular structure to move to the respective between the first or second configurations. The tubular structure can be a braided structure. The members can form an everted tubular sleeve. A proximal end of the outer sleeve is movable relative a proximal end of the inner sleeve. A locking system can fix the introducer sheath at a desired diameter.

23 Claims, 7 Drawing Sheets

(56) References Cited

U.S. PATENT DOCUMENTS

| | | | |
|---|---|---|---|
| 4,946,440 A * | 8/1990 | Hall | 604/164.09 |
| 5,171,305 A * | 12/1992 | Schickling et al. | 604/271 |
| 5,300,048 A | 4/1994 | Drewes, Jr. et al. | |
| 5,364,345 A * | 11/1994 | Lowery et al. | 604/500 |
| 5,662,703 A * | 9/1997 | Yurek et al. | 623/1.12 |
| 6,296,633 B1 * | 10/2001 | Helgerson | 606/1 |
| 6,902,575 B2 * | 6/2005 | Laakso et al. | 623/1.11 |
| 7,435,253 B1 | 10/2008 | Hartley et al. | |
| 8,512,401 B2 * | 8/2013 | Murray et al. | 623/2.11 |
| 2001/0037065 A1 | 11/2001 | Graf et al. | |
| 2001/0044595 A1 * | 11/2001 | Reydel et al. | 604/98.02 |
| 2003/0023204 A1 * | 1/2003 | Vo et al. | 604/103.07 |
| 2003/0135258 A1 * | 7/2003 | Andreas et al. | 623/1.11 |
| 2005/0187570 A1 * | 8/2005 | Nguyen et al. | 606/159 |
| 2005/0209676 A1 * | 9/2005 | Kusleika | 623/1.11 |
| 2006/0173422 A1 * | 8/2006 | Reydel et al. | 604/271 |
| 2008/0281398 A1 * | 11/2008 | Koss et al. | 623/1.12 |
| 2009/0182411 A1 * | 7/2009 | Irwin et al. | 623/1.12 |
| 2010/0057184 A1 | 3/2010 | Randolph et al. | |
| 2011/0034987 A1 | 2/2011 | Kennedy | |

OTHER PUBLICATIONS

Lee, Stuart, "*Handbook of Composite Reinforcements*", published by John Wiley and Sons, 1992, p. 30, 1 page.

European Search Report from related application No. EP 12 275 114.2, dated Dec. 5, 2012, 5 pages.

Patent Examination Report No. 1 for corresponding Australian patent application No. 2012209013 dated Jul. 23, 2013, 3 pages.

* cited by examiner

DELIVERY DEVICE HAVING A VARIABLE DIAMETER INTRODUCER SHEATH

CROSS-REFERENCE TO RELATED APPLICATIONS

This application is a non-provisional application which claims priority to U.S. Provisional Application No. 61/514,241 filed on Aug. 2, 2011, which is incorporated by reference herein in its entirety.

BACKGROUND

The present disclosure relates to a delivery device, including an introducer sheath for deploying, for example, a prosthesis within a body lumen or guiding interventional devices into a body lumen. It also relates to delivery device having an introducer sheath with an adjustable diameter and a mechanism for varying the diameter of the introducer sheath.

Numerous procedures have been developed that involve the percutaneous insertion of a medical device into a body lumen, such as a blood vessel or duct, of a patient's body. Such a device may be introduced into the lumen by a variety of known techniques. For example, a wire guide may be introduced into a blood vessel using the Seldinger technique. This technique involves creating a surgical opening in the vessel with a needle and inserting a wire guide into the vessel through a bore of the needle. The needle can be withdrawn, leaving the wire guide in place. A delivery device is then inserted over the wire guide and into the vessel. The delivery device may be used in conventional fashion to insert into the blood vessel a variety of medical devices, such as catheters, cardiac leads, balloons, stents, stent grafts, and the like.

For example, the delivery device may be used to deliver and deploy an expandable prosthesis, such as a stent graft, at a lesion site to treat a damaged or diseased body lumen such as a bile duct or a blood vessel. A stent graft is usually formed from a tubular body of a biocompatible graft material with one or more stents mounted into or onto the tubular body to provide support therefor. The stents may be balloon expandable stents and/or self-expanding stents. The deployment of the prosthesis into the lumen of a patient from a remote location by the use of an introducer delivery and deployment device is described in, e.g., U.S. Pat. No. 7,435,253 to Hartley entitled "A Prosthesis and a Method and Means of Deploying a Prosthesis," which is incorporated herein by reference in its entirety.

The delivery device is configured to retain the prosthesis in a delivery configuration during delivery to the lesion site. The catheter typically includes an inner cannula spaced from an outer sheath to define a prosthesis retaining region for receiving the prosthesis. The prosthesis is loaded onto an inner cannula along a prosthesis retaining region, with an outer sheath retaining the prosthesis in the delivery configuration. After the delivery device is delivered to the lesion site, the prosthesis may be deployed, for example, with retraction of the outer sheath relative to the inner cannula away from the prosthesis to allow for expansion thereof. Accurate placement of an appropriately sized prosthesis should sufficiently cover the target lesion site for treatment and the ends of the prosthesis should be engaged with healthy tissue of the body lumen.

It would be desirable to load the appropriately sized prosthesis into an delivery device that is as small as possible. Besides the size of the prosthesis being a factor in the size selection of a delivery device, the shape and size of the body lumen can also be important. Thus, introducing a delivery device that is relatively smaller than the body lumen can avoid potential blockage of fluid or blood flow within the lumen, which can adversely affect the lumen and other parts of the body. Furthermore, the body lumen can be tortuous, thus making relatively smaller delivery devices easier to pass through the tortuous portions.

However, relatively smaller delivery devices can be problematic. For instance, substantial shear forces can be created between the prosthesis and the outer sheath when loading and/or deploying the prosthesis. Such substantial shear forces consequently will require higher pushing or retraction forces when attempting to move the outer sheath relative to the prosthesis during loading and/or deploying. The primary cause of the substantial shear forces is due to overpacking of the prosthesis within the annular space between the outer sheath and the inner cannula. For instance, substantially high overpacking can result when the prosthesis occupies greater than 70% of the annular space. Thus, with the desire to deploy a prosthesis as large as possible with an outer sheath as small as possible, such prosthesis can overfill the annular space. Such overfilling provides greater surface area contact between the prosthesis and the outer sheath and less radially inward movement from the prosthesis. In addition, frictional interference with the outer sheath can be greater than the columnar strength of the prosthesis, which can allow for deformation of the prosthesis in the longitudinal direction, thereby collapsing the prosthesis in an accordion-like fashion. Moreover, rigid portions of the prosthesis, such as the stents and/or barbs, may scrape the inner surface of the outer sheath. Scraping can form debris and thus increase the risk of introducing potential emboli into the body. Scraping can also compromise the retaining strength and weaken the outer sheath, which can allow the outer sheath to bulge undesirably to a larger delivery profile.

Thus, there remains a need to facilitate loading and/or deployment of a prosthesis within a delivery device, and in particular, to reduce the shear forces caused between a prosthesis and an introducer sheath. Further, there remains a need for an introducer sheath that can be radially movable between an expandable configuration, e.g., for reduction of shear forces, and a contracted configuration, e.g., for as small as possible delivery profile, multiple times during loading and deployment of the prosthesis and subsequent to deployment.

BRIEF SUMMARY

The present disclosure seeks to provide an improved introducer and method for loading a prosthesis and deploying a prosthesis within a lumen of a body. According to a first aspect, a delivery device includes an introducer sheath that includes an adjustable tubular structure having a wall defining a lumen extending through the tubular structure. The tubular structure is movable between a first configuration and a second configuration. In the first configuration, the tubular structure has a first diameter and a first axial length, and in the second configuration, the tubular structure has a larger second diameter and a shorter second axial length. An actuator can move the tubular structure between the first and second configurations. The actuator can include an inner member and an outer member coupled to one another to surround the tubular structure. The inner member is disposed along an inner wall of the tubular structure. The outer member is disposed along an outer wall of the tubular structure. In response to relative movement between the members and the tubular structure in a first direction, the actuator allows the tubular structure to move to the first configuration, and in a second direction, the actuator allows the tubular structure to move the second configuration.

According to another aspect, a delivery device is provided having a carrier and a prosthesis mounted on a region of the carrier to define a subassembly. The device includes an outer sheath having a passageway extending therein to slidably receive the subassembly. The outer sheath can include an operable member movable between a first position and a second position. The wall of the outer sheath can include an adjustable tubular structure having a proximal end coupled to the operable member and an inner member and an outer member disposed along the respective inner and outer wall of the tubular structure. The proximal end of the corresponding inner and outer members is coupled to the operable member. The distal end of the outer member is coupled to the distal end of the inner member to form an evertable member. In response to movement of the operable member between the first second positions, the proximal end of the inner member and the proximal end of the outer member move relative to one another to selectively change a diameter of the tubular structure.

In yet another aspect, a method of varying a diameter of an introducer sheath, such as for loading and/or deploying a prosthesis, is provided. The method can include one or more of the following steps. A sheath body coupled to a hub assembly are provided. The sheath body can include an inner member and an outer member coupled to one another and surrounding an adjustable tubular structure to define an evertable member. The tubular structure is movable between a first configuration and a second configuration. In the first configuration, the tubular structure has a first diameter and a first axial length, and in the second configuration, the tubular structure has a larger second diameter and a shorter second axial length. The inner and outer members are moved relative to the tubular structure to allow the tubular structure to move between the first configuration and the second configuration to vary the diameter of the tubular structure.

BRIEF DESCRIPTION OF THE DRAWINGS

Embodiments of the present disclosure are described below, by way of example only, with reference to the accompanying drawings, in which.

DETAILED DESCRIPTION OF THE DRAWINGS AND THE PRESENTLY PREFERRED EMBODIMENTS

For the purposes of promoting an understanding of the principles of the present disclosure, reference will now be made to the embodiments illustrated in the drawings, and specific language will be used to describe the same. It is to be understood that the Figures are schematic and do not show the various components in their actual scale. In many instances, the Figures show scaled up components to assist the reader. It should also be noted that in the Figures like-referenced numerals designate corresponding components throughout the different views.

In the following discussion, the terms "proximal" and "distal" will be used to describe the opposing axial ends of the sheath, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

The term "interventional device" refers to any device, object, or structure, that supports, repairs, or replaces, is configured to support, repair, or replace, or that may be used, alone or in combination with other devices, objects, or structures, to support, repair, or replace a body part or a function of that body part. Examples of interventional devices include, but are not limited to, sheaths, catheters, wire guides, cardiac leads, vessel occlusion devices, filters, prostheses, stents, stent grafts, and delivery and deployment devices.

Figure 1:
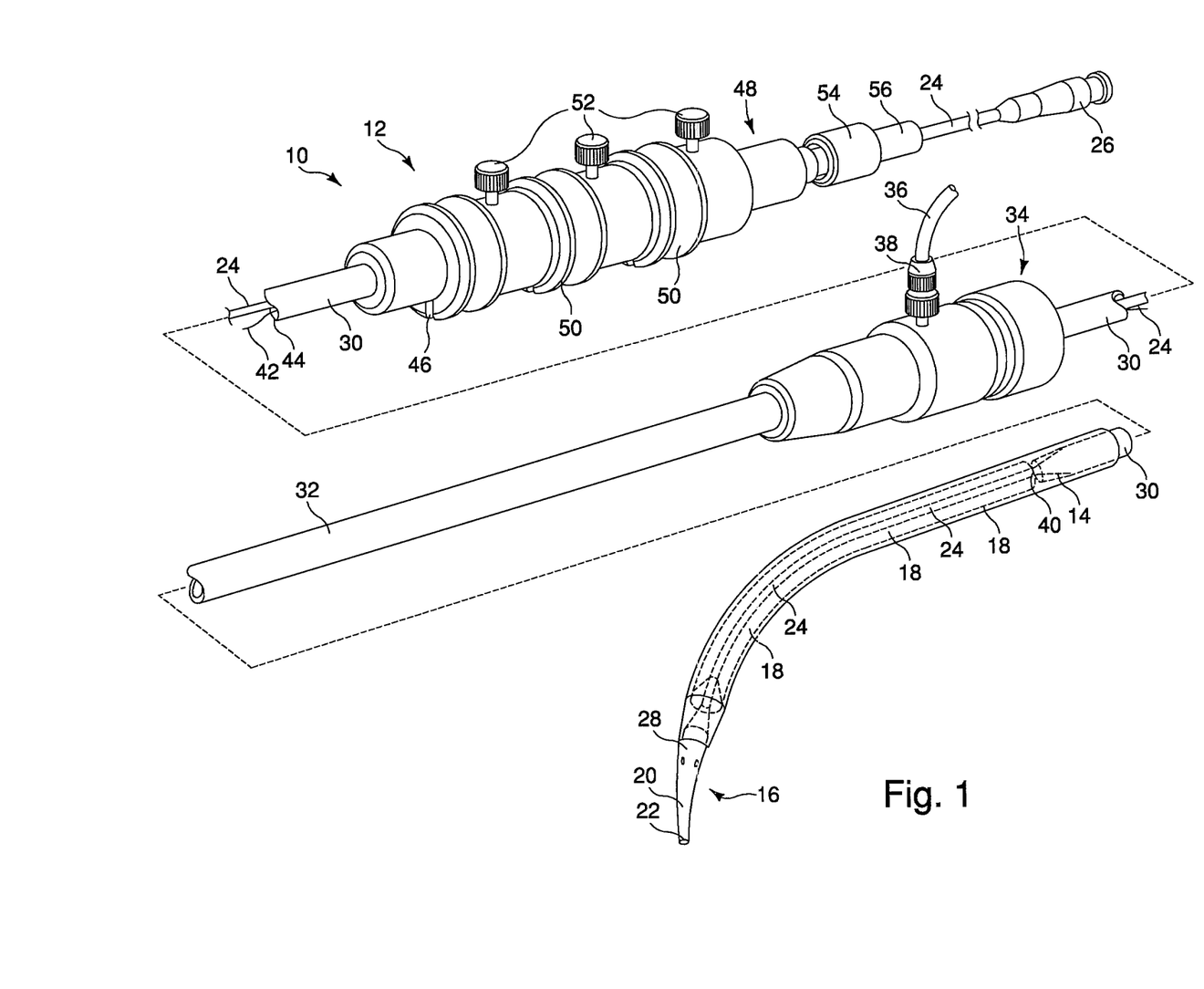
FIG. 1 is a perspective view of an example of a delivery device.

FIG. 1 illustrates one example of a delivery device 10, which can include an external manipulation section 12, a proximal attachment region 14, and a distal attachment region 16. The proximal attachment region 14 and the distal attachment region 16 can secure the two ends of a prosthesis 18. During the medical procedure to deploy the prosthesis 18, the proximal and distal attachment regions 14, 16 can travel through the patient's vasculature, in this example, to a desired deployment site. The external manipulation section 12 at the proximal end of the introducer device 10, which is operated by a surgeon to manipulate the introducer, remains outside of the patient throughout the procedure.

The distal attachment region 16 can include a dilator tip 20, which is typically provided with a bore 22 therein for receiving a guide wire (not shown) of conventional type. The longitudinal bore 22 can also provide a channel for the introduction of medical reagents. For example, it may be desirable to supply a contrast agent to allow angiography to be performed during placement and deployment phases of the medical procedure.

An inner catheter or cannula 24, conventionally made from a flexible thin walled metal tube, can be fastened to the dilator tip 20. The inner catheter 24 is flexible so that the introducer device 10 can be advanced along a relatively tortuous vessel, such as a femoral artery, and so that the distal end of the introducer device 10 can be longitudinally and rotationally manipulated. The inner catheter 24 can form a carrier to carry the prosthesis 18 or other device to be implanted in the patient. The inner catheter 24 can extend through the introducer device 10 to the external manipulation section 12, terminating at a connection device 26, in conventional manner. The connection device 26 is designed to accept a syringe to facilitate the introduction of reagents into the inner catheter 24 and for this purpose is typically provided with a threaded luer lock connection.

Where provided, a pusher sheath or rod 30 (hereinafter referred to as a pusher member), typically made from a plastics material, can be mounted coaxial with and radially outside of the inner catheter 24. The pusher member 30 may be "thick walled," that is; the overall outer profile of its wall is preferably several times greater than that of the inner catheter 24. In some instances, the pusher member 30 and the inner catheter 24 can be the same component, possibly having different outer diameters at the location at which the prosthesis 18 is to be carried. The pusher member 30 and the inner catheter 24 can extend proximally to the external manipulation region 12.

An outer sheath 32 can be extended coaxially over and radially outside of the pusher member 30. The prosthesis 18, which may be a stent, a stent graft or any other implant or prosthesis deliverable by the introducer device 10, can be retained in a compressed condition by the outer sheath 32. The outer sheath 32 can extend proximally to a sheath manipulator and hemostatic sealing unit 34 of the external manipulation section 12. The unit 34 may include a hemostatic seal (not shown) and a side tube 36 held to the unit 34 by a conventional luer lock 38.

The sheath manipulator and hemostatic sealing unit 34 may also include a clamping collar (not shown) that clamps the outer sheath 32 to the unit 34 and a sealing member such as a silicone seal ring (not shown) forms the hemostatic seal around the pusher member 30. The side tube 36 can facilitate the introduction of medical fluids, such as, e.g., saline solution, between the pusher member 30 and the outer sheath 32.

During assembly of the introducer device 10, the outer sheath 32 can be advanced over the proximal end of the dilator tip 20 of the distal attachment region 16 while the prosthesis 18 is held in a compressed state by an external force. A suitable proximal retention section (not visible in this view) can be coupled to the pusher member 30 and can retain a proximal end of the prosthesis 18 during the procedure. The distal end of the prosthesis 18 may be provided with a loop of material (not shown) through which a distal restraining wire 42 can be extended. The distal restraining wire 42 can also extend through an aperture (not shown) in the proximal attachment section 14 into an annular space 44 defined between the inner catheter 24 and the pusher member 30. The distal restraining wire 42 can extend through the annular space 44 to the manipulation region 12 and can exit the annular space 44 at a distal wire release mechanism 46.

A proximal portion of the external manipulation section 12 can include at least one restraining wire actuation section 50 mounted on a body 48, in turn mounted onto the pusher member 30. The inner catheter 24 may pass through the body 48. The distal wire release mechanism 46 and the proximal wire release mechanism 50 can be mounted for slidable movement on the body 48. Clamping screws 52 can prevent inadvertent early release of the implant 18. A hemostatic seal (not shown) is included so that the release wires can extend out through the body 48 without unnecessary blood loss during the medical procedure.

A proximal portion of the external manipulation section 12 can include a pin vice 54 mounted onto the proximal end of the body 48. The pin vice 54 can have a screw cap 56. When screwed in, vice jaws (not shown) of the pin vice 54 can clamp against or engage the inner catheter 24. When the vice jaws are engaged, the inner catheter 24 can only move with the body 48 and hence it can only move with the pusher member 30. With the screw cap 56 tightened, the entire assembly can be moved together as one piece.

Once the introducer device 10 is in the desired deployment position, the outer sheath 32 is withdrawn and the proximal and distal wire release mechanisms 50, 46 are released to allow the prosthesis 18 to expand. For some procedures, the sheath 32 may be left in place after expansion of the prosthesis 18. The pusher member 30 and inner catheter 24 may be withdrawn and replaced by a further interventional device, using the indwelling outer sheath 32 as a guide.

One component of introducer devices is an introducer sheath. Introducer sheaths having a tubular structure that is radially movable between expanded and contracted configurations to a desired diameter are described herein. This arrangement can be useful, e.g., when loading an interventional device, when deploying an interventional device, and/or when allowing an interventional device to pass therethrough. In the contracted configuration, the tubular structure has a first diameter and a first axial length. In the expanded configuration, the tubular structure has a larger second diameter and a shorter second axial length. A sleeve actuator can move the tubular structure between the first and second configurations. The sleeve actuator can include an inner sleeve and an outer sleeve, which may form an everted tubular sleeve. In response to relative movement between the outer and inner sleeves and the tubular structure in a first or second direction, the sleeve actuator allows the tubular structure to move to the respective contracted or expanded configuration, or any position therebetween.

Figure 2:
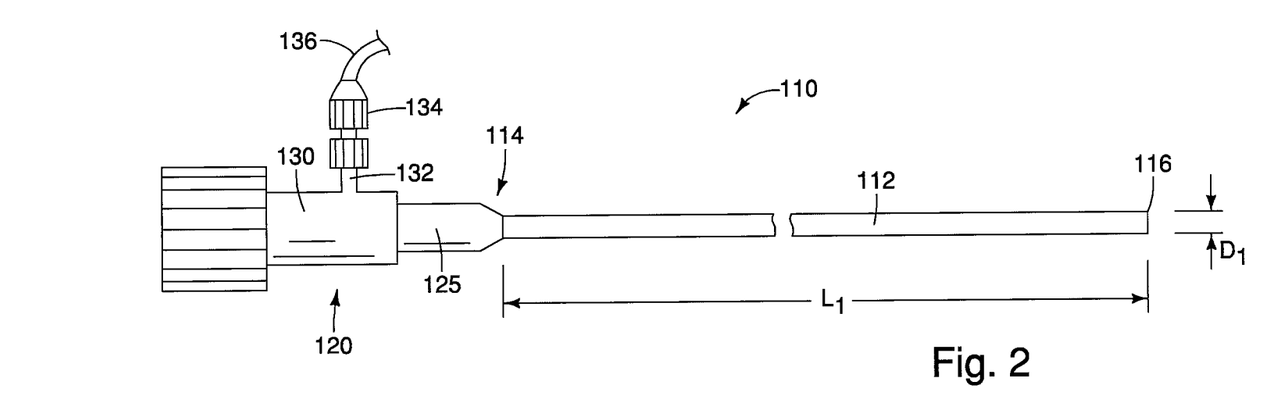
FIG. 2 is a side view of one example of an introducer sheath in a contracted configuration.
Figure 3:
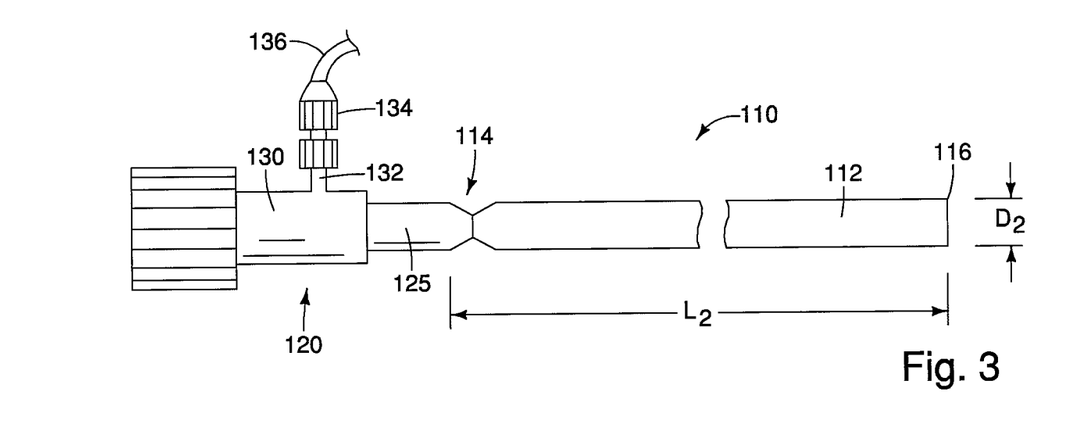
FIG. 3 is a side view of one example of an introducer sheath in an expanded configuration.

FIGS. 2-3 illustrate one example of an introducer outer sheath 110 of a delivery device having a sheath body 112 that is movable between a first, contracted configuration and a second, expanded configuration, respectively. The introducer sheath 110 can be provided with the introducer device 10 in place of the outer sheath 32, or can be used separately from the introducer device. In the contracted configuration, the sheath body 112 has a first diameter D1 and a first axial length L1. In the expanded configuration, the sheath body 112 has a larger second diameter D2 and a shorter second axial length L2. The sheath body 112 has a proximal end 114 and a distal end 116. A hub assembly 120 can be coupled to the proximal end 114 of the sheath body 112. The hub assembly 120 can include a sheath manipulator 125 to operatively move the sheath body 112 between the contracted and expanded configurations. The hub assembly 120 can include a hemostatic sealing unit 130, which includes a sealing member (not shown) to form a seal around a device extending therethrough, such as the pushing member 30 or another interventional device. The hemostatic sealing unit 130 can include a side port 132 having a coupling end such as a luer lock 134 for fluid connection to a tube 136. The tube 136 can facilitate the introduction of medical fluids, such as saline solution, e.g., in the annular space between the pusher member 30 when provided and the sheath body 110. One example of the hemostatic sealing unit is the CAPTOR™ Valve, which is commercially available from Cook Medical, Inc. (Bloomington, Ind.).

Figure 4A:
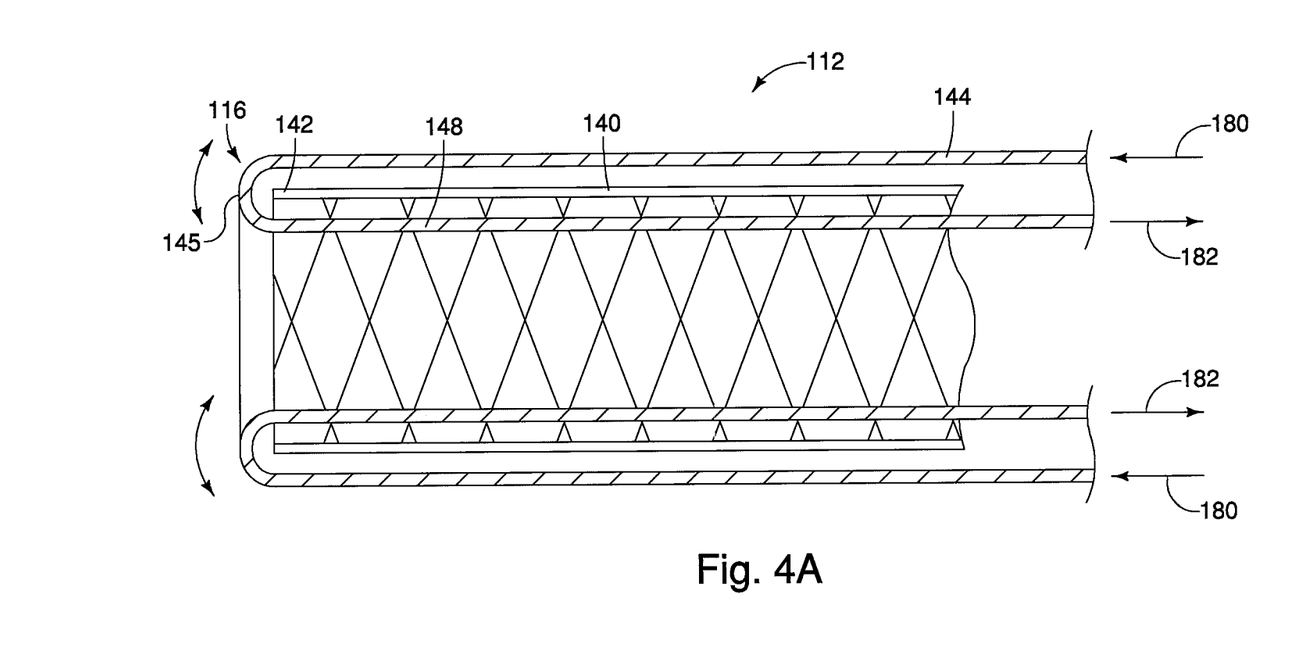
FIG. 4A is a cross-sectional view of a sheath body provided with an introducer sheath.
Figure 5:
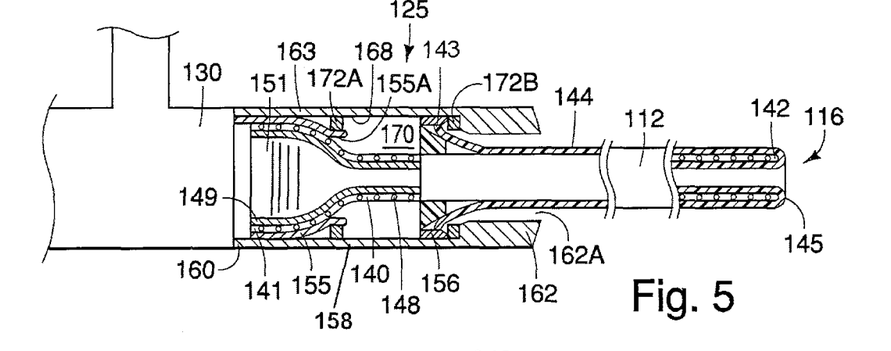
FIG. 5 is a partial cross-sectional view of a sheath manipulator and a sheath body provided with an introducer sheath.

FIGS. 4A and 5 illustrate an exemplary wall construction of the sheath body 112. The sheath body 112 can include an adjustable tubular structure 140, and outer and inner members such as an outer sleeve 144, and an inner sleeve 148. The tubular structure 140 is capable of providing the expansion and contraction properties to the sheath body 112. In other words, the tubular structure 140 can provide mechanical support for the sheath body 112 when radially moving between the contracted and expanded configurations. Thus, the tubular structure 140 is contractible and expandable to vary the diameter and length of the sheath body 112. In one example, the tubular structure 140 is a passive device that requires another structure or actuator to actuate movement of the tubular structure 140. In another example, the tubular structure 140 is an active device having a spring or biasing force such that the tubular structure has a relaxed configuration or biased in the contracted or expanded configuration. For instance, the tubular structure 140 can be biased to return automatically to its contracted configuration when the tubular structure is presently not in the contracted configuration. The tubular structure 140 can include many structures such as a braided filament, a spiraled member, a coiled member, or other structures known in the art to mechanically move in the radial direction.

In one example, the tubular structure 140 can be formed from a mesh material, braided or woven filament mesh, to permit the tubular structure to move between the contacted and expanded configurations. In one embodiment, the tubular structure 140 is a braided structure made of braided or interwoven materials, wires, ribbons, fibers, strands, yarns, monofilaments, multi-filaments, or other known configuration, or collectively known as "filaments," as will be used in the specification. The filament materials can include polypropylene, polyester, polyethylene, polyamide (nylon), polyamide copolymers, silicone, polyurethane, or other biocompatible elastomers. The filament materials can also be metal, such as stainless steel, titanium, alloys including a nickel-titanium alloy, a nickel-cobalt alloy, another cobalt alloy, tantalum, shape-memory materials, such as nitinol. The filament materials can have various cross-sectional shapes such as circular, oval, rectangular, square, or other geometric shapes known in the art.

The filament material in a braided pattern can provide sufficient radial column strength to the sheath body 112 when in the contracted or expanded configuration. Filaments are braided in a biaxial braid sometimes referred to as "Chinese finger trap" braid. The braided filaments extend in a helix configuration along a longitudinal axis of the sheath body, with a first set of filaments having a common direction of winding but axially displaced relative to each other, and crossing a second set of filaments axially displaced relative to each other but having an opposite direction of winding. The first and second sets of filaments can cross each other at a first angle with respect to the longitudinal axis when the net force along the length of the braided structure is zero. This is due to the constraint set by the filaments to move the tubular structure 140 to either the contracted or expanded configuration. The braided angle can increase to a second angle relative to the longitudinal axis at minimum radial compression (maximum shortening) when an axial force is applied along the length of the tubular structure 140.

Any number of filaments of any size, such as 0.15-0.6 mm diameter, can be interwoven into helical shape strands on a mandrel of a suitable diameter. The first set of filaments (one-half of the total number) are helically wound clockwise and the second set of filaments (one-half) are helically wound counterclockwise such that each clockwise filament is adjacent and interbraided with a counterclockwise filament. The filaments can be helically wound at the first angle $\alpha 1$ such that the relationship is represented by the following equation: $\cos(\alpha 1) = A/B$. A is defined as wN—where N is the number of carriers and w is the width of the filaments, whereas B is defined as $2\Pi(1-\sqrt{1-F})D$—where D is the diameter of the tubular structure 140 and F is the fraction of projected area covered by filaments (1.0-0.5). This equation is described in *Handbook of Composite Reinforcements* by Stuart Lee (John Wiley and Sons (1992)), which is incorporated herein by reference in its entirety. The filaments of the tubular structure 140 can be coupled to one another at least at its proximal end ends such as by adhesive, soldering, welding, polymer coated, while the remaining intermediate portion of the tubular structure 140, including the distal end remains free to move radially accordingly. The tubular structure 140 can be heat treated, such as an annealing process, to set the desired braided configuration at rest. The tubular structure may be coated with a polymer to fill the spacings between the braided filaments. The polymer coating can be flexible to move radially and axially with the adjustable tubular structure. The tubular structure may remain uncoated to allow for a greater freedom of movement between the filaments, which can reduce the amount of force to move the adjustable tubular structure.

The outer sleeve 144 is disposed along the length of the outside surface of the tubular structure 140 to protect the wall of the body lumen from any moving components of the tubular structure. The inner sleeve 148 is disposed along the length of the inside surface of the tubular structure to provide a solid walled conduit for fluid and/or interventional devices. The outer sleeve 144 and the inner sleeve 148 are coupled to one another to form an everted sleeve member as shown in the figures to surround the tubular structure 140. The point of eversion 145 of the sleeves is located at the distal end 142 of the tubular structure 140. The material for the outer sleeve 144 and/or the inner sleeve 148 can be same as each other or different from one another so long as the material is flexibility and resilient to accommodate changes (increase or decrease) in the diameter and the length of the tubular structure 140. For example, the material can be elastomeric materials such as silicone, urethane, or rubber, although any suitable composition known in the art for such purposes may be substituted. Alternative materials include polytetrafluoroethylene (PTFE); polyamide (e.g., nylon 12) material, a polyamide block copolymer (e.g., PEBA) and blends thereof (e.g., nylon 12/PEBA and PEBA/PEBA blends); polyolefins, polyolefin copolymers and blends thereof; polyesters (e.g., poly(ethylene terephthalate), PET); polyurethane copolymers with MDI, HMDI or TDI hard segment and aliphatic polyester, polyether or polycarbonate soft segment (e.g., Pellethane, Estane or Bionate); and polyester copolymers with 4GT (PBT) hard segment and aliphatic polyester or polyether soft segments (e.g., Hytrel, Pelprene or Arnitel)). The materials for the inner sleeve and/or the outer sleeve may be reinforced with fibers to strengthen the sleeves during axial tension.

In one example, the outer sleeve 144 and the inner sleeve 148 are integrally formed from a single tubular sleeve. In another example, the outer sleeve 144 and the inner sleeve 148 are each tubular sleeves coupled to one another in an end-to-end fashion by an attachment mechanism, such as adhesives, welding, soldering, heat bonding, sewing, or other attachment mechanism known in the art. In another example, the outer sleeve and the inner sleeve are longitudinal members that are strips of material rather than tubular sleeves. The outer surface of the outer sleeve 144 and/or an inner surface of the inner sleeve 148 may have a lubricious coating. The lubricious surface can allow interventional devices to pass through the sheath body 112 and/or the sheath body 112 to pass through a body vessel more effectively. For example, a lubricious coating, such as silicone liquid coating or other coatings have lubricious properties known in the art, can be applied to the surface. Alternatively, a lubricious film, such as fluoropolymer, hydrogel, or other films having lubricious properties known in the art can be used.

In FIG. 5, the distal end of the hemostatic sealing unit 130 may have a smaller diameter portion 151. The smaller diameter portion 151 can be used for attaching the unit 130 to a proximal end 149 of the inner sleeve 148 and/or a proximal end 141 of the tubular structure 140 by an attachment mechanism, such as mechanical interference fit, adhesives, welding, soldering, heat bonding, or other attachment mechanism known in the art. In this example, the proximal end 149 of the inner sleeve 148 can be flared and can attach to the smaller diameter portion 151 in a secured relationship. The proximal end 141 of the tubular structure 140 can be flared and can attach to the smaller diameter portion 151 over the proximal end 149 of the inner sleeve 148 in a secured relationship. A cap 155 can fit over the proximal ends 141, 148 to maintain sufficient contact pressure between the proximal ends 141, 149 and thesmaller diameter portion 151 for a secured fit to the hemostatic sealing unit 130. The end opening 155A of the cap 155 can be sized to the diameter of the sheath body when in the expanded configuration. In other words, when the sheath body 112 is in the contracted configuration, a small gap may exist between the inner edge of the end opening 155A and the outer surface of the sheath body, as shown in FIG. 5. The end opening 155A can be modified to maintain contact with the sheath body 112 during movement of the sheath body between the expanded and contracted configurations. For example, a sleeve, such as a flexible sleeve made from an elastomer, can be placed at the end and can maintain contact with the sheath body regardless of its diameter.

The proximal end 145 of the outer sleeve 144, which may be flared, can be attached to a ring support 156 in a secured relationship by an attachment mechanism, such as adhesives, welding, soldering, heat bonding, or other attachment mechanism known in the art. The proximal end 145 of the outer sleeve 144 can be axially spaced in the distal direction from the proximal end 149 of the inner sleeve 148. This arrangement can allow for relative axial movement between the proximal end 143 of the outer sleeve 144 and the proximal end 149 of the inner sleeve 148. Such relative movement between the outer and inner sleeves permits the movement of the tubular structure 140 between the contracted and expanded configurations. It is desirable that the sheath body 112 is configured to remain as flexible as possible to permit passage through tortuous portions of the body lumen. To this end, it is preferable that the sheath body 112 is provided without any longitudinal members, struts, stiffening members, or stylets that interface with the tubular structure in a manner to actuate movement of the tubular structure. Such longitudinal members may increase the stiffness of the sheath body and thus may minimize the capability of the sheath body to pass through tortuous vessels.

To facilitate such relative movement between the outer and inner sleeves, the sheath manipulator 125 can include a cannula housing 158. The cannula housing 158 can be fitted over the respective proximal ends of the sleeves and the tubular structure between the hemostatic sealing unit 130 and the sheath body 112. The cannula housing 158 can include a proximal end 160 adjacent the hemostatic sealing unit 130 and a distal end 162 having an end opening 162A disposed about the sheath body 112. The cannula housing 158 may have a uniform diameter or may be tapered from the proximal end 160 to the distal end 162. The cannula housing may also have a sleeve therearound to improve grippability. The end opening 162A of the housing 158 can be sized to the diameter of the sheath body 112 when in the expanded configuration. In other words, when the sheath body 112 is in the contracted configuration, a small gap may exist between the inner edge of the end opening 162A and the outer surface of the sheath body, as shown in FIG. 5. The end opening 162A can be modified to maintain contact with the sheath body during movement of the sheath body between the expanded and contracted configurations. For example, a sleeve, such as an elastomeric sleeve, can be placed at the end. The sleeve can appear tapered between the housing and the outer surface of the sheath body. The sleeve may be more flexible than the body 163 in order to maintain close contact with the sheath body during movement of the sheath body. In other words, the end opening 162A of the cannula housing 158 may be configured to contract and expand with movement of the sheath body between the contracted and expanded configurations.

The inner surface 168 of the cannula housing 158 can define an inner cavity 170. The ring support 156 can be in slidable engagement with the inner surface 168 of the cannula housing. The ring support 156 can be configured to remain substantially perpendicular to the longitudinal axis of the sheath body 112 during sliding movement. One or more physical stops, such as two physical stops 172A, 172B, in the form of protrusions or internal rings or ribs, can be attached to or formed along the inner surface 168 and axially spaced from one another. The physical stops 172A, 172B can limit travel of the ring support 156 between a first position and a second position (shown in FIG. 5), which define the maximum expanded configuration and the maximum contracted configuration of the sheath body 112, respectively. The stops can limit the relative position between the proximal end 143 of the outer sleeve 144 and the proximal end 149 of the inner sleeve 148 between the two extents during sliding movement. To this end, when the ring support 156 is at the first, proximal physical stop 172A, the proximal end 143 of the outer sleeve is in close proximity to the proximal end 149 of the inner sleeve and the sheath body is in the expanded configuration. When the ring support 156 is at the second, distal physical stop 172B, the proximal end 143 of the outer sleeve is farther away from the proximal end 149 of the inner sleeve and the sheath body is in the contracted configuration, as shown in FIG. 5. In one example, the ring support can travel about 2 cm in order to achieve a French size change of about 4 French, although the these dimensions can be changed in order to achieve a desired configuration.

With additional reference to FIG. 4A, the movement of the sheath body 112 between the contracted and expanded configurations is illustrated. To contract the sheath body 112, the end user can actuate the ring support 156 in a distal direction toward the second physical stop 172B. This causes distal movement of the outer sleeve 144 in a first direction, represented by arrows 180, relative to the inner sleeve 142, which may be fixed, and inversion of the sleeves at the point of eversion 145. The point of eversion 145 of the sleeves can then be removed from applying an axial compressive force to the tubular structure 140 to permit contraction of the tubular structure 140. For example, when the tubular structure 140 is a braided structure, the braided filaments rotate relative to one another to decrease the braided angle therebetween. As a result, the diameter of the tubular structure 140 is contracted and the length of the tubular structure is increased. It is contemplated that when the tubular structure has a bias in the contracted configuration, removal of the force at the distal end 142 can allow the tubular structure 140 to automatically return to the contracted configuration.

To expand the sheath body 112, the end user can actuate the ring support 156 in a proximal direction toward the first physical stop 172A. This causes proximal movement of the outer sleeve 144 in a second direction, represented by arrows 182, relative to the inner sleeve 142 and eversion of the sleeves at the point of eversion 145. The point of eversion 145 of the sleeves can then apply an axial compressive force to the tubular structure 140, which causes the tubular structure to shorten and expand. For example, when the tubular structure is a braided structure, the braided filaments rotate relative to one another to increase the braided angle therebetween. As a result, the diameter of the tubular structure is expanded and the length of the tubular structure is reduced. It is contemplated that when the tubular structure has a bias in the expanded configuration, removal of the axial force from the distal end 142 can allow the tubular structure 140 to automatically return to its expanded configuration.

Figures 4B, 4C:
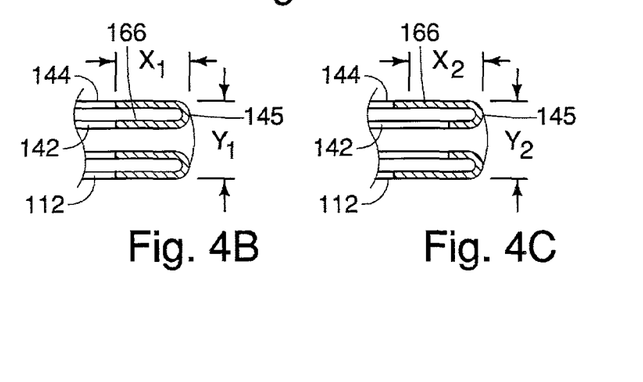
FIGS. 4B-4C depict one example of a sheath body with radiopaque material.

According to FIGS. 4B-4C, the sheath body 112 may have a radiopaque material 166 formed therein to indicate under fluoroscopy or other imaging techniques the size and configuration of the sheath body. Nonlimiting examples of radiopaque materials include silver, gold, platinum, tantalum, tungsten, or various forms of derivate alloys thereof. In FIG. 4B, the sheath body 112 is in the contracted configuration. The radiopaque material 166 is applied to the inner sleeve 142 and the outer sleeve 144 such that the radiopaque overlays itself and appears to a first length X1 and a first diameter Y1. When the sheath body 112 is moved toward the fully expanded configuration, the radiopaque material will appear to increase to a second length X2 and increase in diameter to a second diameter Y2. Construction of a polymer layer with a radiopaque material is described in U.S. Pat. No. 5,300,048 and U.S. Patent Publ. No. 2001/0037065, each of which is incorporated herein by reference in its entirety. It can be recognized by one skilled in the art that with modifications the radiopaque material can appear to decrease, instead of increase, in length and/or in diameter. Regardless, the radiopaque material can aid the clinician in determining the precise configuration of the sheath body.

Figure 6:
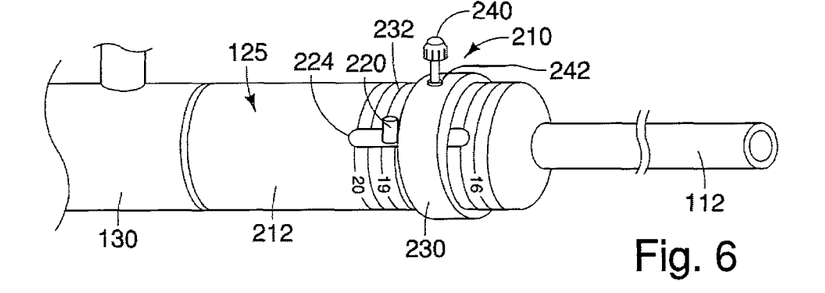
FIG. 6 is a perspective view of a sheath manipulator and a locking system provided with an introducer sheath.

FIG. 6 depicts the sheath manipulator 125 can be provided with a locking system 210 to selectively position the ring structure within the cannula housing 212 at any intermediate position between the first and second physical stops. This can allow the end user to expand and contract the sheath body 112 to different diameters between the maximum and minimum diameters. The locking system 210 can include a trigger element 220 extending outwardly from a slot 224 formed in the cannula housing 212. A sealing member (not shown) may be provided at the slot 224 to surround the trigger element 220 and prevent leakage from within the cannula housing. The trigger element 220 may be coupled to the ring structure (internal within the cannula housing) in a manner such that movement of the trigger element 220 corresponds with movement of the ring structure. The end user may directly apply force to the trigger element 220 in order to move the ring structure to a location for the desired diameter of the sheath body. The end user can then maintain the position of the trigger element 220 within the slot 224 in order to maintain the diameter of the sheath body. Visual indication of the radial size of the sheath body, such as, e.g., 16 French (F), 17 F, 18 F, 19 F, and 20 F, may be provided on the surface of the cannula housing. The ends of the slot 224 may function as the physical stops, instead of or in addition to, the internal protrusions or ribs shown in FIG. 5.

In one example, the locking system 210 may include a movable collar 230. The collar 230 may be coupled to the trigger element 220 so that the position of the trigger element within the slot is maintained. FIG. 6 depicts the collar 230 in an abutting relationship with the trigger element 220 on the proximal side of the trigger element, although the collar can be placed on the distal side. It is contemplated that the collar 230 may be attached to the trigger element in a manner such that movement of the collar 230 directly corresponds with movement of the trigger element. The collar 230 can be fitted over the cannula housing 212 and can be threadably engaged with the cannula housing 212. For example, the collar 230 can have internal threads and the cannula housing 212 can have external threads 232. The threads engage with one another such that the collar 212 can move axially in either the proximal or the distal direction relative to the cannula housing 212 by rotation in the corresponding direction. The threaded engagement can provide precise control of the diameter of the sheath body 112 in various increments of conventional French sizes and positions in between conventional French sizes. A pin vise 240 can be disposed on the collar 230 to lock the position of the collar 230 in a fixed position relative to the cannula housing 212. The pin vise 240 includes a threaded shaft engaged with a threaded opening 242 formed in the collar 230. An enlarged head may be included on the pin vise to provide a more effective grippable surface for the end user. The pin vise 240 can be rotated in a tightening direction to position the end of the pin vise into frictional contact with the cannula housing 212, where such pressure prevents any movement of the collar 230 relative to the cannula housing 212 and any movement of the trigger element 220. The pin vise 240 can be rotated in a loosening direction to remove the end of the pin vise away from frictional contact with the cannula housing 212 to permit relative movement between the collar 230 and the cannula housing 212 and movement of the trigger element 220.

In another example, the collar may move over the cannula housing 212 by sliding instead of rotation. For instance, the external threads 232 may be ratcheting grooves formed in the cannula housing. The pin vice 240 may be a spring loaded pawl. The pawl may be biased in a locking position to position the end of the pawl into frictional contact with the grooves of the cannula housing 212, where such pressure prevents any movement of the collar 230 relative to the cannula housing 212 and any movement of the trigger element 220. The pawl can be withdrawn to an unlocking position to remove the end of the pawl away from frictional contact with the cannula housing 212 to permit relative axial movement between the collar 230 and the cannula housing 212 and movement of the trigger element 220.

Figure 7:
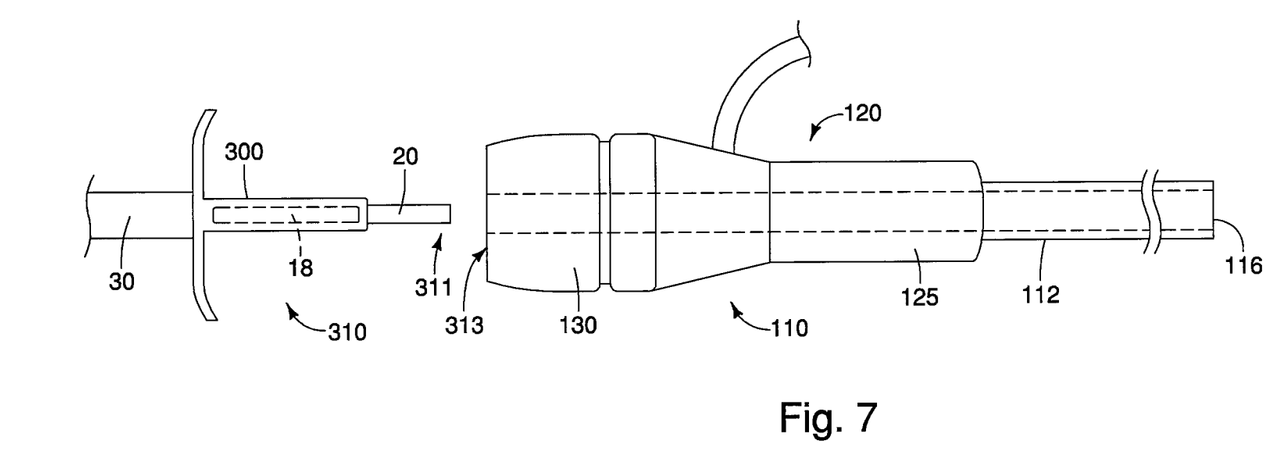
FIG. 7 illustrates a method of varying the diameter of an introducer sheath during loading of a prosthesis.

One example of the advantageous use of the introducer sheath 110 is during loading of a prosthesis into the introducer device. In FIG. 7, a segment of the inner cannula (not shown) can be inserted within a medical device, such as the prosthesis 18 (shown in dashed lines), that is entirely constrained in a radially compressed configuration by a removable retainer sheath 300. One or more of the inner cannula, the pusher member 30, the dilator tip 20, and the prosthesis 18 retained by the retainer sheath 300 can define a subassembly 310. A distal end 311 of the subassembly 310 can be inserted within a proximal end 313 of the introducer sheath 110 through the hub assembly 120. During insertion, the retainer sheath 300 is removed from the prosthesis 18 so that the prosthesis 18 is to be retained in the radially compressed configuration by the sheath body 112. According to FIG. 7, before insertion or during insertion, the sheath body 112 can be moved to the expanded configuration, such as, e.g. to a size of about 20 French, to minimize shear forces or friction between the inner surface of the sheath body and the prosthesis 18 that is placed against the inner surface. This can reduce the risk of axial movement and/or deformation of the prosthesis during loading, as well as scraping of the inner surface by the prosthesis. The subassembly 310 can be translated within the expanded sheath body 112, with the pushing member 30 pushing the prosthesis 18 toward the distal end 116 of the sheath body 112. The distal end 116 of the sheath body 112 is then aligned to a desired location relative to the dilator tip 20. At this moment, the prosthesis 18 would occupy about 60-80% of the annular space between the outer sheath body 112 and the inner cannula. The sheath body 112 can then be moved to the contracted configuration as described herein, such as, e.g., about 16 French, to set the delivery position of the prosthesis 18 and reduce the profile of the sheath body 112 before being introduced to the body lumen. Consequently, the annular space volume is reduced and the prosthesis 18 would occupy about 90-95% of the annular space between the outer sheath body 112 and the inner cannula.

Figure 8A:
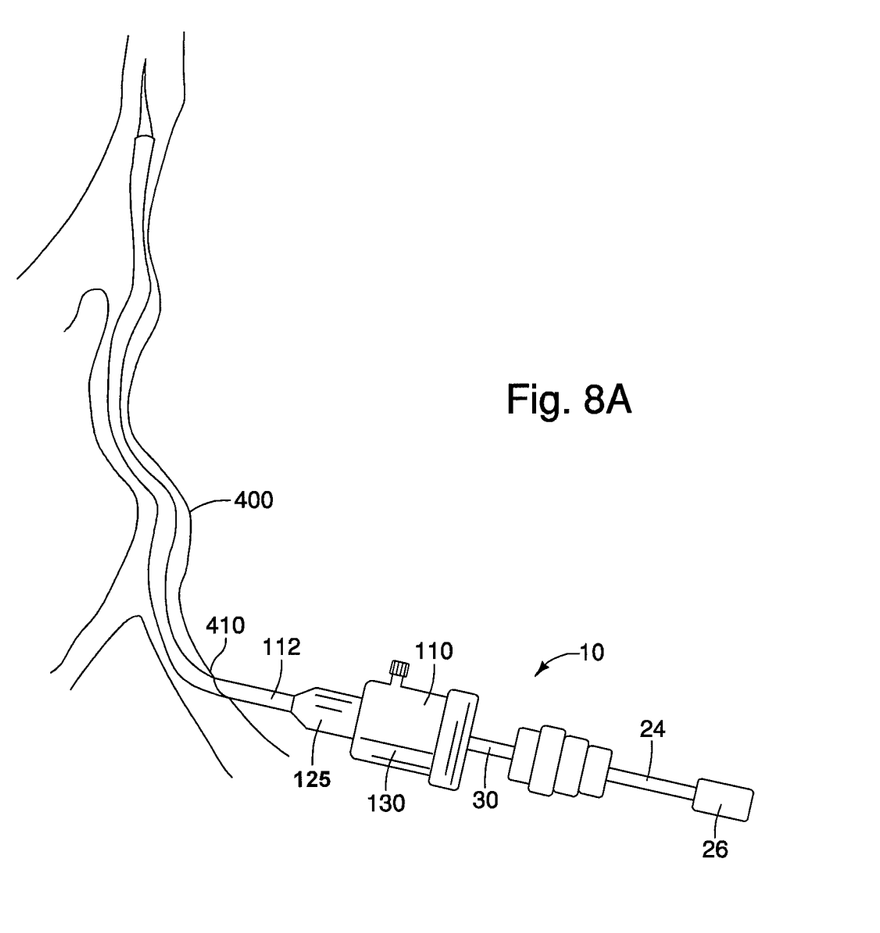
FIGS. 8A-8D illustrate a method of varying the diameter of an introducer sheath within a body lumen.

FIGS. 8A-8D illustrate another example of use of the introducer sheath 110, with the subassembly 310 which together define the introducer device 10, during deployment of a medical device, such as the prosthesis 18, into a lumen of a body structure 400, such as artery, vein, duct, or other tubular passageway in the body. The introducer sheath 112 can be introduced into the body lumen without the subassembly as can be appreciated by those skilled in the art. The introducer device 10 may be used to percutaneously insert into the body lumen 400 a variety of medical devices, such as catheters, cardiac leads, balloons, prostheses, stents, stent grafts, and the like. For example, a wire guide may be introduced into the body lumen 400 using the Seldinger technique. This technique involves creating a surgical opening 410 in the body lumen 400 with a needle and inserting a wire guide into the body lumen 400 through a bore of the needle. The needle can be withdrawn, leaving the wire guide in place. In FIG. 8A, the introducer device 10 is then inserted over the wire guide and into the body lumen 400. In one example, the introducer device 10 may be used to deliver and deploy an expandable prosthesis 18. The introducer device 10 is translated through the body lumen 400 such that a distal end of the introducer device 10 is positioned at a treatment site within the body lumen. It is desirable that the sheath body 112 is configured to remain as flexible as possible to permit passage through tortuous portions of the body lumen.

Figure 8B:
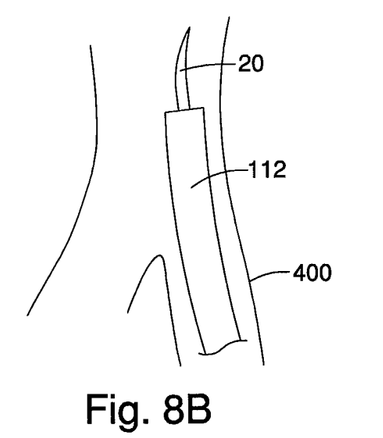
Figure 8C:
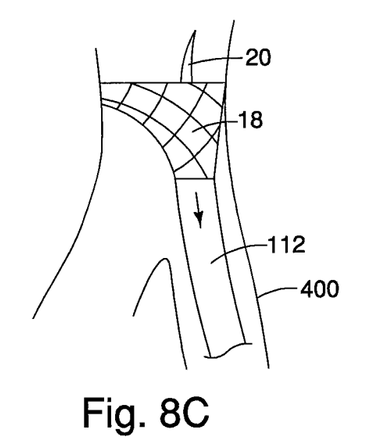
Figure 8D:
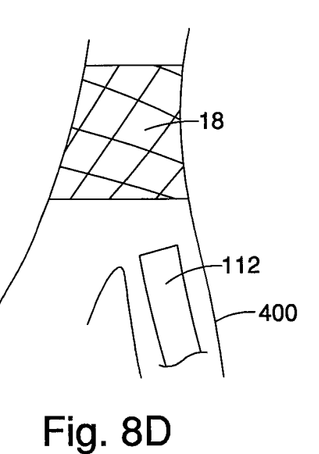

The prosthesis can then be deployed at the treatment site. In FIG. 8B, before deployment, the sheath body 112 can be moved to the expanded configuration as described herein. This can minimize the shear forces or friction typically caused by the prosthesis placed against the inner surface of the sheath body 112, thereby reducing the amount of force used by the end user to either retract the sheath body 112 or push the pusher member. For example, in FIG. 8C, retraction of the sheath body 112 in the expanded configuration relative to the prosthesis 18 can allow for expansion of the prosthesis at the treatment site. Alternatively, the pusher member can be used to push the prosthesis from the distal end of the sheath body to allow for expansion of the prosthesis. After deployment of the prosthesis 18, the dilator tip 20, the inner catheter 24, the pusher member 30, and anything else besides the introducer sheath 110 can be removed from the body, as shown in FIG. 8D. The sheath body 112 may remain at any position between the expanded and contracted configurations for removal from the body after its initial use. In addition, after its initial use, the sheath body 112 can remain in an expanded configuration to permit the subsequent passage of other medical devices and/or interventional devices therethrough into the body lumen. The sheath body may also be moved to another target site within the body. After its final use, such as for introduction of subsequent devices, the sheath body 112 can be removed from the body.

The features of the various embodiments described above and their modifications may be substituted for or combined with one another as desired. It is also to be understood that the various features of the dependent claims appended hereto may be used with one another in any desired combination of those claims.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A delivery device comprising an introducer sheath, the introducer sheath comprising:
   a carrier having an elongated body, and a prosthesis mounted on a region of the carrier;
   an adjustable tubular structure having a wall defining a lumen extending through the tubular structure, the tubular structure being movable between a first configuration and a second configuration, wherein in the first configuration the tubular structure has a first diameter and a first axial length, and in the second configuration the tubular structure has a larger second diameter and a shorter second axial length; and
   an actuator to move the tubular structure between the first and second configurations, the actuator comprising an inner member and an outer member coupled to one another to surround the tubular structure, the inner member disposed over an inner wall of the tubular structure, the outer member disposed over an outer wall of the tubular structure, the outer and inner members movable relative to the tubular structure, wherein in response to relative movement between the members and the tubular structure in a first direction, the actuator allows the tubular structure to move to the first configuration, and in a second direction, the actuator allows the tubular structure to move to the second configuration.

2. The introducer sheath of claim 1, wherein the tubular structure comprises a braided structure.

3. The introducer sheath of claim 1, wherein the tubular structure has a biasing force and is biased in the first configuration.

4. The introducer sheath of claim 1, wherein the tubular structure comprises a distal end, and the actuator comprises a tubular sleeve everted around the distal end of the tubular structure at an eversion point to define the inner and outer members, wherein the eversion point is operative to apply an axial force to the distal end of the tubular structure in response to relative movement between the outer and inner members and the tubular structure in the second direction.

5. The introducer sheath of claim 1, wherein each of the outer and inner members comprises a proximal end, the proximal end of the inner member axially spaced from the proximal end of the outer member.

6. The introducer sheath of claim 5, wherein the proximal end of the inner member is fixed, and the proximal end of the outer member is movable relative the fixed proximal end of the inner member.

7. The introducer sheath of claim 6 further comprising a hub assembly coupled to the tubular structure, the inner member, and the outer member.

8. The introducer sheath of claim 7, wherein the tubular structure comprises a proximal end, and the proximal end of the tubular structure and the proximal end of the inner member are coupled to a distal end of the hub assembly.

9. The introducer sheath of claim 8 further comprising a cannula housing coupled to the distal end of the hub assembly.

10. A delivery device comprising an introducer sheath, the introducer sheath comprising:

an adjustable tubular structure having a wall defining a lumen extending through the tubular structure, the tubular structure being movable between a first configuration and a second configuration, wherein in the first configuration the tubular structure has a first diameter and a first axial length, and in the second configuration the tubular structure has a larger second diameter and a shorter second axial length;

an actuator to move the tubular structure between the first and second configurations, the actuator comprising an inner member and an outer member coupled to one another to surround the tubular structure, the inner member disposed along an inner wall of the tubular structure, the outer member disposed along an outer wall of the tubular structure, the outer and inner members movable relative to the tubular structure, a hub assembly coupled to the tubular structure, the inner member, and the outer member and a cannula housing coupled to the distal end of the hub assembly, wherein in response to relative movement between the members and the tubular structure in a first direction, the actuator allows the tubular structure to move to the first configuration, and in a second direction, the actuator allows the tubular structure to move to the second configuration, wherein each of the outer and inner members comprises a proximal end, the proximal end of the inner member axially spaced from the proximal end of the outer member, wherein the proximal end of the inner member is fixed, and the proximal end of the outer member is movable relative the fixed proximal end of the inner member, and wherein the tubular structure comprises a proximal end, and the proximal end of the tubular structure and the proximal end of the inner member are coupled to a distal end of the hub assembly, and wherein the proximal end of the outer member is coupled to a ring support that is slidable within the cannula housing.

11. The introducer sheath of claim 10, wherein the cannula housing comprises a slot formed therein, and the ring support comprises a trigger element extending outwardly through the slot.

12. The introducer sheath of claim 11 further comprising a collar movably coupled to the cannula housing, and a lockable pin coupled to the collar to fix the relative position between the collar and the cannula housing.

13. The introducer sheath of claim 1, wherein the outer and inner members are unattached to the tubular structure and remain slidable along the respective walls of the tubular structure in both of the first and second directions to selectively move the tubular structure to a desired diameter.

14. A delivery device comprising:
a carrier having an elongated body, and a prosthesis mounted on a region of the carrier to define a subassembly; and
an outer sheath having a passageway extending therein, the passageway configured to slidably receive the subassembly, the outer sheath comprising an operable member movable between a first position and a second position, an adjustable tubular structure having a wall defining a lumen extending through the tubular structure, the tubular structure having a proximal end coupled to the operable member, an inner member disposed over an inner wall of the tubular structure, the inner member having a proximal end coupled to the operable member and a distal end, and an outer member disposed over an outer wall of the tubular structure, the outer member having a proximal end coupled to the operable member and a distal end coupled to the distal end of the inner member to form an evertable member;
wherein in response to movement of the operable member between the first and second positions, the proximal end of the inner member and the proximal end of the outer member move relative to one another to selectively change a diameter of the tubular structure.

15. The introducer device of claim 14, wherein the outer sheath further comprises a cannula housing, and the operable element comprises a ring structure coupled to the proximal end of the outer member, and slidably movable relative to the cannula housing.

16. The introducer device of claim 15, wherein the operable element comprises a locking system to selectively fix the position of the ring structure relative to the cannula housing such that the diameter of the tubular structure is selectively fixed.

17. The introducer device of claim 14, wherein the tubular structure has a biasing force and is biased in the contracted configuration.

18. The introducer device of claim 17, wherein the tubular structure comprises a distal end, and the evertable member comprises a tubular sleeve everted around the distal end of the tubular structure at an eversion point,
wherein in response to movement of the operable element toward the first position, the tubular structure is allowed to move to the contracted configuration, and
wherein in response to movement of the operable element toward the second position, the eversion point applies an axial force to the distal end of the tubular structure to shorten and radially expand the tubular structure.

19. A method of varying a diameter of an introducer sheath, comprising:
providing a sheath body coupled to a hub assembly, the sheath body having an inner member and an outer member coupled to one another and surrounding an adjustable tubular structure to define an evertable member, the tubular structure being movable between a first configuration and a second configuration, wherein in the first configuration the tubular structure has a first diameter and a first axial length, and in the second configuration the tubular structure has a larger second diameter and a shorter second axial length; and
moving the inner and outer members relative to the tubular structure to allow the tubular structure to move between the first configuration and the second configuration to vary the diameter of the tubular structure.

20. The method of claim 19 further comprising locking the position of the evertable member relative to the tubular structure to fix the diameter of the tubular structure.

21. The introducer sheath of claim 9, wherein the proximal end of the outer member is coupled to a ring support that is slidable within the cannula housing.

22. The introducer sheath of claim 21, wherein the cannula housing comprises a slot formed therein, and the ring support comprises a trigger element extending outwardly through the slot.

23. The introducer sheath of claim 22, further comprising a collar movably coupled to the cannula housing, and a lockable pin coupled to the collar to fix the relative position between the collar and the cannula housing.

* * * * *